United States Patent [19]

Drewlow

[11] Patent Number: Plant 6,307

[45] Date of Patent: Sep. 27, 1988

[54] IMPATIENS PLANT NAMED SUNDAZZLE

[75] Inventor: Lyndon W. Drewlow, Ashtabula, Ohio

[73] Assignee: Mikkelsens, Inc., Ashtabula, Ohio

[21] Appl. No.: 916,566

[22] Filed: Oct. 8, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

An Impatiens plant named Sundazzle, having rose-red and white bicolored flowers; long broad medium green, non-variegated leaves, vigorous, compact, self-branching growth habit; floriferous habit, and having tolerance to low light and low temperature conditions.

2 Drawing Sheets

1

The present invention relates to a new and distinctive cultivar of Impatiens plant, botanically known as Impatiens, and referred to by the cultivar name Sundazzle. Sundazzle was developed by me through controlled breeding by crossing Mikkelsen Seedling No. 84-1743-4 (seed parent) with Mikkelsen Seedling No. 84-1743-1 (pollen parent). Asexual reproduction of the progeny of the stated cross by terminal or stem cuttings performed by me in Ashtabula, Ohio has shown that unique features of this new impatiens are stabilized and are reproduced true to type in successive propagations.

The following characteristics distinguish the new impatiens from both its parent varieties and other cultivated impatiens of this type known and used in the floriculture industry. In certain instances the characteristics are compared with similar characteristics of other cultivars. Of the cultivars referred to, Astro is disclosed in U.S. Plant Pat. No. 4,691, and Sunregal, Sunglow, Sunburst, and Twilight are disclosed in pending applications.

1. Sundazzle has a distinct rose-red and white bicolor flower which is similar in pattern to Sunglow, Sunregal, and Sunburst. Twilight is only slightly bicolored, and Astro is bicolored only on the upper petal.

2. Sundazzle has a red stem tinged with green, with the stem being lighter in color than Sunburst, Astro and Sunglow. Twilight and Sunregal have almost purple stems.

3. Flower size of Sundazzle is smaller than Astro, Twilight and Sunregal, similar to Sunburst, and larger than Sunglow.

4. Sundazzle is similar in plant size and shape to Sunburst, while Sunglow is larger but with the same mounded shape. Sunregal is more upright and larger in size. Both Astro and Twilight are more upright, open and taller plants.

5. Sundazzle has no variegation on its leaf, similar to Sunregal. Sunburst has a very small amount of variegation along the midrib near the base of the leaf. Astro, Sunglow and Twilight are heavily variegated.

6. Sundazzle has large broad leaves which are similar to Sunburst, Twilight and Astro. Sunregal and Sunglow both have much smaller leaves.

7. Sundazzle has dark yellow green leaves with a purple tinge, similar to Sunburst. Astro has more purple in the dark green leaf part. Twilight and Sunglow are a dull dark green with almost no purpling, while Sunregal has a dark shiny green leaf.

2

8. Sundazzle has two flowers per leaf axil, similar to Sunregal, Sunglow and Sunburst. Astro and Twilight have only one flower per leaf axil.

9. Sundazzle is highly self-branched, compact, vigorous, and very floriferous, making it suitable for 4" pots, hanging baskets and bedding plant use.

10. Flowering of Sundazzle is 6 to 10 days earlier than Astro and Twilight, 2 to 5 days earlier than Sunglow and similar to Sunregal and Sunburst. Sundazzle has the ability to flower under low light and 70° F. without dropping leaves or losing flower size.

In the accompanying colored photographs, sheet 1 is a top perspective view of Sundazzle, showing colors as true as it is reasonably possible to obtain in a colored reproduction of this type. Sheet 2 is an enlarged color photograph showing the bicolored flowers.

The following is a detailed description of Sundazzle based on plants produced under commercial practices in Ashtabula, Ohio under both greenhouse and outdoor conditions. The photographs were taken of greenhouse grown plants in early June. Color references are made to the Royal Horticultural Society Colour Chart except where general terms of ordinary dictionary significance are used.

Parentage: A controlled cross between Mikkelsen Seedling No. 84-1743-4 and Mikkelsen Seedling No. 84-1743-1.

Propagation:

(A) *Type cutting.*—Stem 15 mm long will develop to 4 to 5 cm long in 18 to 21 days.

(B) *Time to root.*—8 to 10 days at 23° C. summer, and 10 to 12 days at 20° C. winter.

(C) *Rooting habit.*—Heavy, fibrous.

Plant description:

(A) *Form.*—Compact, self-branching, symmetrically mounded, greenish red-stemmed, vigorous flowering herb.

(B) *Habit of growth.*—Vigorous, self-branching, compact, mounded, continuous flowering once it has started; flowers above foliage.

(C) *Foliage description.*—Large broad dark yellow green leaves with reddish midrib; no variegation on the leaf. (1) Size: 9 to 11 cm long and 3.0 to 3.5 cm wide. (2) Shape: Lanceolate with acuminate apex and acute base. (3) Texture: Upper side rugose and lower side glabrous. (4) Margin: Finely serrated with fine cilia. (5) Color: Young foliage top side 146A. Under side: 187A. Mature foliage top side 148A. Under side: Between 187A and B. (6) Venation: Pinnate; reddish midrib and few major veins.

Flowering description:

(A) *Flowering habits.*—Flowers continuously from leaf whorl in progressively orderly manner taking 5 to 7 days from large bud to bloom. Each leaf axil has two flower buds and the secondary flower buds in a leaf whorl do not start to open until all primary ones open in that whorl. Before all the secondary flowers have bloomed in a whorl, the primary flowers of the whorl above start to open. Flowers can last from 2 to 3 weeks.

(B) *Natural flowering season.*—Indeterminant and continuous. Quantity of flowering increases with increasing levels of light.

(C) *Flower buds.*—Ellipsoidal, flowers perfect, green spur 3.0 to 3.5 cm long on a mature bud with throat behind ovary and originating from the major sepal.

(D) *Flowers borne.*—On individual short green pedicels 3.5 cm at maturity from a whorl of 6 leaves; flowering progressively around the whorl with all primary flowers in a whorl opening before the secondary ones start to open; flowers both above and in the canopy of leaves.

(E) *Quantity of flowers.*—Very floriferous due to the two flowers per leaf axil; flowering development is continuous with tight buds and mature flowers being present at the same time.

(F) *Petals.*—(1) Shape: Heart shaped with the upper petal larger in size than the rest. (2) Color: Top side in summer when opening, 47A and 36D, fading to 47B and 155C; underside 46D with the middle of the underside of the upper petal being 43B; under side of rest of petals 48C to D. (3) Number of petals: Five (5) in number. (4) Size of flowers: 4 to 4.5 cm in diameter.

(G) *Reproductive organs.*(1) Stamens: Five (5) in number. (a) Anther shape: Hooded, color cream with reddish tint. (B) Pollen color: Cream. (2) Pistels: (a) Stigma: Segmented column shaped, color purple. (b) Style color: Purple. (c) Ovaries: Five (5) in number, celled, 5 mm in size before fertilization, color purple.

Disease resistance: No significant disease or insect problems noted to date.

I claim:

1. A new and distinct Impatiens plant named Sundazzle, as described and illustrated, and particularly characterized by its rose-red and white bicolored flowers; long broad medium green, non-variegated leaves; vigorous, compact, self-branching growth habit; floriferous habit, and tolerance to low light and low temperature conditions.

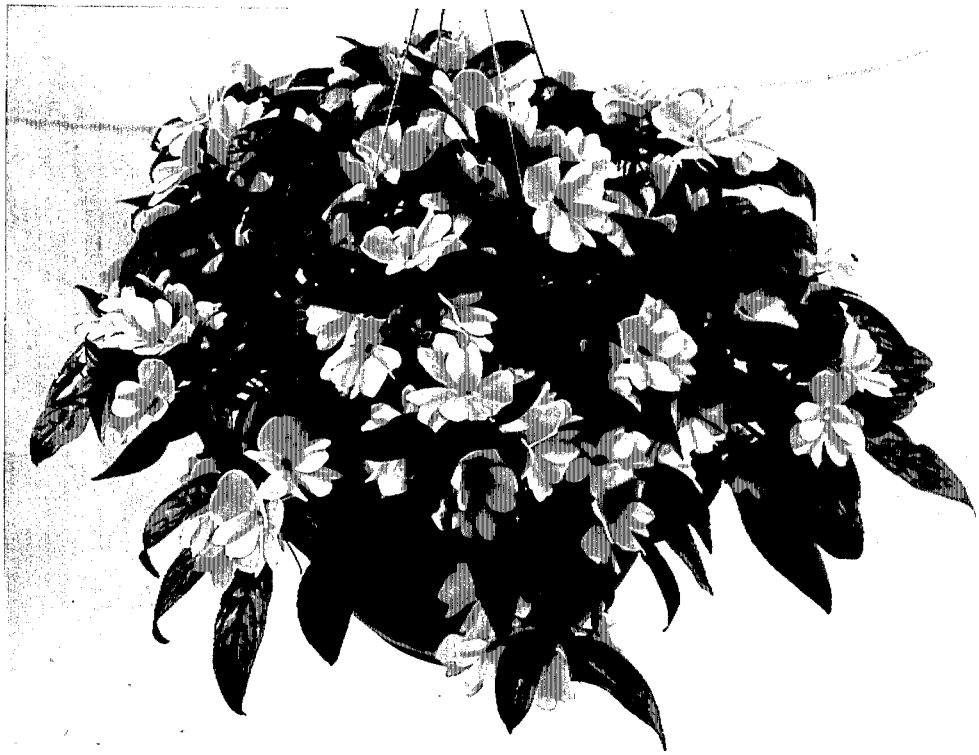

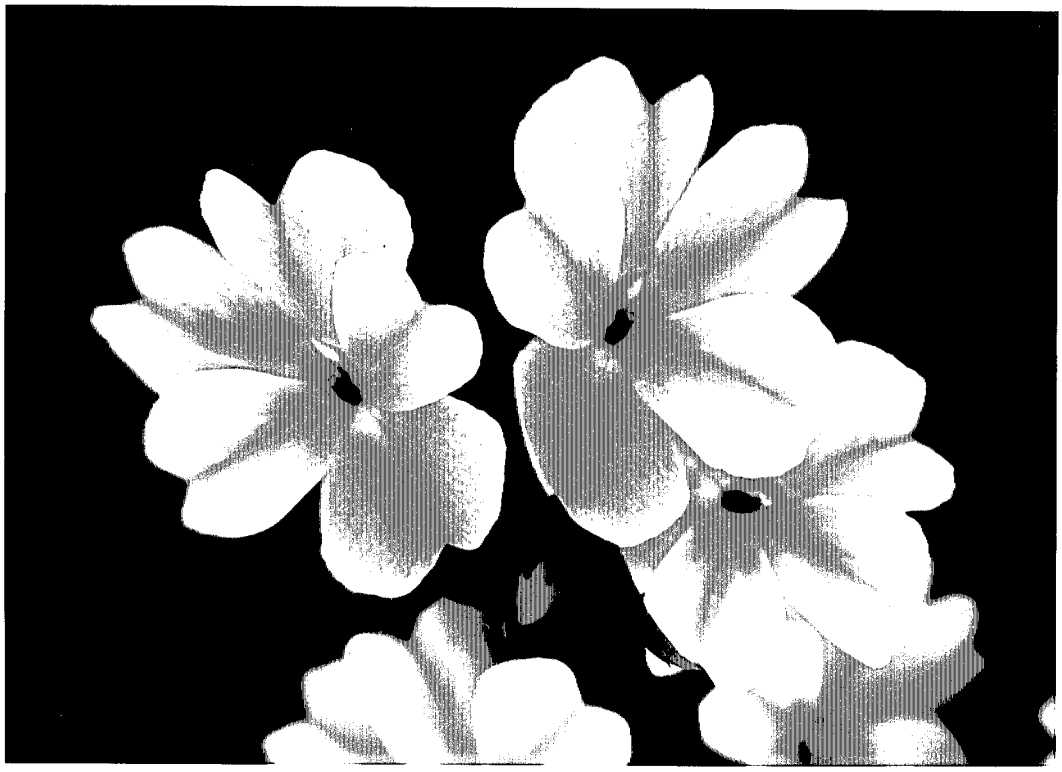

* * * * *